United States Patent [19]

Malherbe et al.

[11] 4,226,999
[45] Oct. 7, 1980

[54] PIPERIDYL ESTERS OF PHENOLALKYLENE CARBOXYLIC ACIDS

[75] Inventors: Roger Malherbe, Muttenz; Michael Rasberger, Riehen, both of Switzerland

[73] Assignee: Ciba-Geigy Corporation, Ardsley, N.Y.

[21] Appl. No.: 1,195

[22] Filed: Jan. 5, 1979

Related U.S. Application Data

[62] Division of Ser. No. 751,775, Dec. 16, 1976, Pat. No. 4,148,784.

[30] Foreign Application Priority Data

Dec. 29, 1975 [CH] Switzerland ............... 16820/75
Nov. 19, 1976 [CH] Switzerland ............... 14580/76

[51] Int. Cl.³ ............................................. C07D 211/46
[52] U.S. Cl. ........................................ 546/222; 546/22; 546/24; 546/188; 546/190; 546/207; 546/216; 546/223; 546/224; 546/230; 546/235; 546/238; 546/239; 546/242
[58] Field of Search ............... 546/222, 224, 238, 188, 546/190, 239, 216, 207, 24, 22, 230, 223, 235; 260/45.8 N

[56] References Cited

U.S. PATENT DOCUMENTS

| | | | |
|---|---|---|---|
| 3,992,390 | 11/1976 | Holt et al. | 546/222 |
| 4,075,165 | 2/1978 | Soma et al. | 546/222 X |
| 4,148,784 | 4/1979 | Malherbe et al. | 546/222 X |

*Primary Examiner*—Henry R. Jiles
*Assistant Examiner*—Richard A. Schwartz
*Attorney, Agent, or Firm*—Wenderoth, Lind & Ponack

[57] ABSTRACT

A compound of the formula I

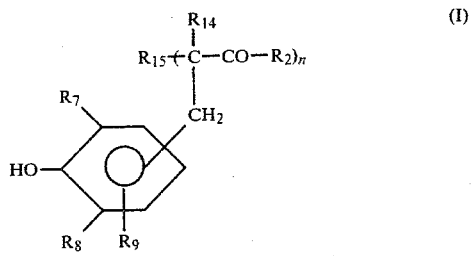

in which $R_2$ is an optionally substituted 4-piperidinyl bonded via oxy or imino, or an optionally substituted 2-(piperidino)-ethoxy, n is 1 or 2, $R_7$ and $R_8$ are hydrocarbon radicals, $R_9$ is hydrogen or methyl, $R_{14}$ is cyano, $-CH_2OH$, a hydroxymethyl which is C-substituted by an optionally substituted 4-piperidinyl bonded via oxy or imino, or by an optionally substituted 2-(piperidino)-ethoxy, or $R_{14}$ is also acyl or nitro, and, when n=1, $R_{15}$ is hydrogen, a substituted hydroxybenzyl, an optionally substituted hydrocarbon radical, an optionally substituted 4-piperidinyl, or alkylene which is optionally linked to $R_{14}$ and optionally substituted, or, when n=2, $R_{15}$ is a direct bond or an optionally interrupted hydrocarbon radical, and its salts as stabilizers for organic material.

3 Claims, No Drawings

PIPERIDYL ESTERS OF PHENOLALKYLENE CARBOXYLIC ACIDS

This application is a division of application Ser. No. 751,775, filed Dec. 16, 1976, now U.S. Pat. No. 4,148,784, issued Apr. 10, 1979.

The present invention relates to new phenols, their manufacture and their use as stabilisers and to organic material which, with the aid of these compounds, has been stabilised against thermooxidative and/or light-induced degradation.

A large number of phenolic antioxidants which are derived from hydroxybenzylated malonic acid derivatives and structures of a similar type are known, for example compounds of the dioctadecyl (4-hydroxy-3,5-di-tert.-butyl-benzyl)-malonate type from U.S. Pat. No. 3,830,828 or compounds of the diethyl 2-(4-hydroxy-3-methyl-5-tert.-butylbenzyl)-2-benzyl-malonate type from German Offenlegungsschrift No. 1,815,894. In addition to these compounds, which contain only one hydroxybenzyl radical in the molecule, those which contain two hydroxybenzyl radicals per molecule are also known, for example 1,3-bis-(3,5-di-tert.-butyl-4-hydroxyphenyl)-(2-carboethoxy-2-phosphonic acid diethyl ester)-propane from British patent specification No. 1,262,557; compare also German Offenlegungsschrift No. 2,216,811, or ethyl 2,2-bis-(4-hydroxy-3-methyl-5-tert.-butyl-benzyl)-2-phenylsulphonyl-acetate, also from the last-mentioned German Offenlegungsschrift, and compounds of the methyl α-cyano-α-(3,5-di-tert.-butyl-4-hydroxybenzyl)-β-(3,5-di-tert.-butyl-4-hydroxyphenyl)-propionate type from British patent specification No. 1,295,432, the ethyl ester of this compound being known from U.S. Pat. No. 3,646,110 and from German Offenlegungsschrift No. 2,216,811, and also methyl α-acetyl-α-(3,5-di-tert.-butyl-4-hydroxybenzyl)-β-(3,5-di-tert.-butyl-4-hydroxyphenyl)-propionate, which is also known from German Offenlegungsschrift No. 1,817,109, and the ethyl ester thereof, which is also known from German Offenlegungsschrift No. 2,216,811. With compounds of this type, the antioxidant action, such as is determined, for example, with correspondingly stabilised polypropylene in the oven ageing test at 149° C., is not adequate for many practical applications. The object of the invention was to provide compounds which have better antioxidative properties, as shown in the above oven ageing test.

According to the invention this is achieved by modifying the ester group of the compounds of the above state of the art and in particular the compounds concerned are esters derived from compounds of the 2,2,6,6-tetrasubstituted 4-hydroxy-piperidine type. In general, esters of this 4-hydroxy-piperidine are known as excellent light protection agents, for example from U.S. Pat. No. 3,640,928, and esters with hydroxybenzylated malonic acids are also known from German Offenlegungsschrift No. 2,456,864. On the other hand, however, the esters according to the invention are distinguished by their antioxidative action and this could not be foreseen.

According to the invention, the compounds concerned are compounds of the formula I

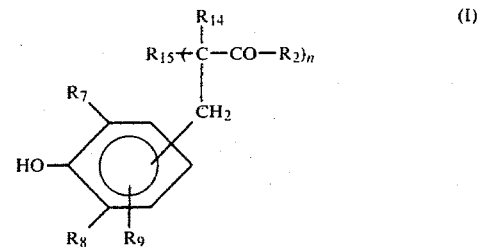

in which $R_2$ is an optionally substituted 4-piperidinyl bonded via oxy or imino, or an optionally substituted 2-(piperidino)-ethoxy, n is 1 or 2, $R_7$ and $R_8$ are hydrocarbon radicals, $R_9$ is hydrogen or methyl, $R_{14}$ is cyano, —CH$_2$OH, a hydroxymethyl which is C-substituted by an optionally substituted 4-piperidinyl bonded via oxy or imino, or by an optionally substituted 2-(piperidino)-ethoxy, or $R_{14}$ is also acyl or nitro, and, when n=1, $R_{15}$ is hydrogen, a substituted hydroxybenzyl, an optionally substituted hydrocarbon radical, an optionally substituted 4-piperidinyl, or alkylene which is optionally linked to $R_{14}$ and optionally substituted, or, when n=2, $R_{15}$ is a direct bond or an optionally interrupted hydrocarbon radical, and their salts.

The invention relates in particular to compounds of the formula I

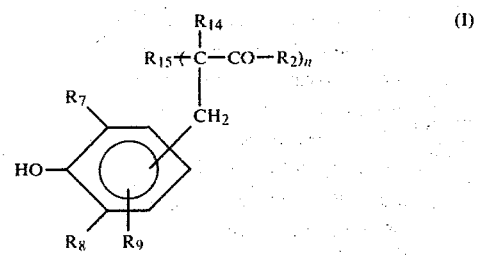

in which $R_2$ is a radical of the formula Ia or Ib

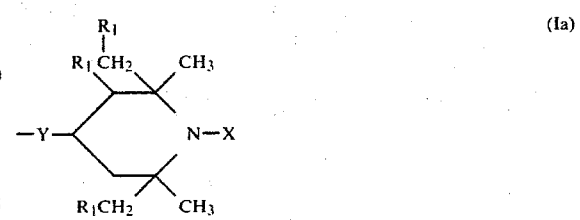

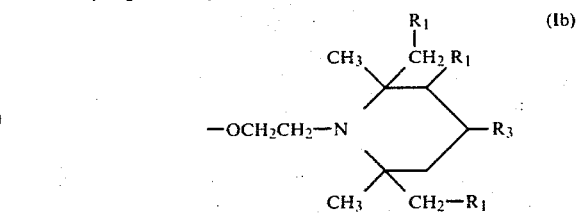

n is 1 or 2, Y is oxy or imino, $R_1$ is hydrogen or $C_1$-$C_5$-alkyl, $R_3$ is hydrogen, —OR$_4$, —NR$_5$R$_6$ or a radical of the formula Ic

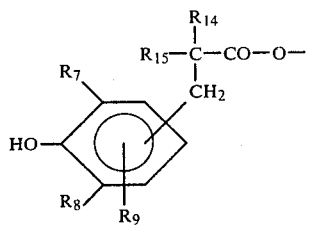

(Ic)

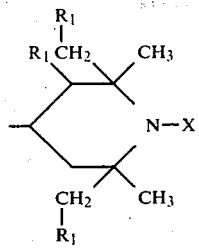

(III)

in which $R_{15}$ is monovalent, $R_4$ is alkyl with 1–18 C atoms, $C_3$–$C_6$-alkenyl, $C_3$–$C_6$-alkinyl, benzyl, 2-cyanoethyl or an aliphatic, cycloaliphatic, aromatic or araliphatic acyl group which has 1–18 C atoms and can be substituted in the aromatic part by halogen, $C_1$–$C_4$-alkoxy, $C_1$–$C_4$-alkyl and/or hydroxyl, $R_5$ is $C_1$–$C_{18}$-alkyl, $C_3$–$C_8$-alkenyl or $C_7$–$C_9$-phenylalkyl, $R_6$ is an aliphatic, cycloaliphatic, aromatic or araliphatic acyl group which has 1–18 C atoms and can be substituted in the aromatic part by halogen, $C_1$–$C_4$-alkoxy, $C_1$–$C_4$-alkyl and/or hydroxyl, $R_7$ and $R_8$ independently of one another are $C_1$–$C_9$-alkyl, $C_7$–$C_9$-aralkyl or $C_5$–$C_8$-cycloalkyl, $R_9$ is hydrogen or methyl, X denotes hydrogen, oxyl, $C_1$–$C_{12}$-alkyl, $C_3$–$C_6$-alkenyl, $C_3$–$C_4$-alkinyl, $C_2$–$C_{21}$-alkoxyalkyl, $C_7$–$C_8$-aralkyl, 2,3-epoxypropyl, an aliphatic acyl group with 1–18 C atoms, $C_1$–$C_{12}$-alkylaminocarbonyl, di-($C_1$–$C_{12}$)-alkylaminocarbonyl, anilinocarbonyl or one of the groups —$CH_2COOR_{10}$, —$CH_2$—$CH(R_{11})$—$OR_{12}$ or —$COOR_{13}$, in which $R_{10}$ is $C_1$–$C_8$-alkyl, $C_3$–$C_6$-alkenyl, phenyl, $C_7$–$C_8$-aralkyl or cyclohexyl and $R_{11}$ is hydrogen, methyl or phenyl and $R_{12}$ denotes hydrogen, an aliphatic or aromatic, araliphatic or alicyclic acyl group with 1–18 C atoms, in which the aromatic part can optionally be substituted by chlorine, $C_1$–$C_4$-alkyl, $C_1$–$C_8$-alkoxy and/or by hydroxyl, and $R_{13}$ denotes $C_1$–$C_{12}$-alkyl, cyclohexyl, phenyl or benzyl, $R_{14}$ is cyano, —$CH_2OH$, —$CH(OH)R_2$, —$COOC_{1-4}$-alkyl, —$CHO$, —$CO$-$R_{16}$, —$SO_2$—$R_{17}$, —$SOR_{17}$, —$P(=O)(OR_{18})_2$ or nitro, in which $R_{16}$ and $R_{17}$ are $C_1$–$C_{17}$-alkyl, phenyl, $C_7$–$C_9$-alkylphenyl, $C_{11}$–$C_{14}$-(hydroxy)-(alkyl)phenyl or $C_{12}$–$C_{16}$-(hydroxy)(alkyl)phenylalkyl, or $R_{16}$ is a radical bonded to $R_{15}$, and $R_{18}$ is $C_1$–$C_{18}$-alkyl, phenyl or allyl, and, if n is 1, $R_{15}$ is hydrogen, a radical of the formula II

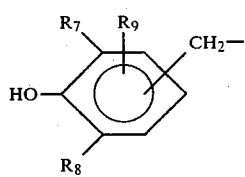

(II)

in which $R_7$, $R_8$ and $R_9$ have the above meaning, or $C_1$–$C_{20}$-alkyl or a $C_1$–$C_{10}$-alkyl which is substituted by phenoxy, $C_7$–$C_{10}$-alkylphenoxy, benzyloxy, cyclohexyloxy, phenylthio, $C_7$–$C_{10}$-alkylphenylthio, $C_2$–$C_{13}$-alkanoyl, cyano, —$C(=O)OR_{19}$, —$O$—$C(=O)R_{20}$ or —$P(=O)(OR_{21})_2$, in which $R_{19}$ is $C_1$–$C_{18}$-alkyl, $C_5$–$C_{12}$-cycloalkyl or a radical of the formula III in which $R_1$ and X have the above meaning and $R_{20}$ is $C_1$–$C_{17}$-alkyl, $C_5$–$C_{12}$-cycloalkyl, phenyl or $C_7$–$C_9$-phenylalkyl and, in the last two radicals, the phenyl parts can be substituted by one or two $C_1$–$C_4$-alkyls and/or hydroxyls, and $R_{21}$ is $C_1$–$C_8$-alkyl, allyl or phenyl, and $R_{15}$ is also $C_2$–$C_{22}$-alkyl which is interrupted by —O—, —S—, —SO— or —$SO_2$—, or is $C_3$–$C_{18}$-alkenyl, $C_3$–$C_8$-alkinyl, $C_5$–$C_{12}$-cycloalkyl, $C_6$–$C_{18}$-alkylcycloalkyl, $C_6$–$C_{14}$-cycloalkylalkyl, $C_7$–$C_{19}$-aralkyl, $C_7$–$C_{19}$-alkylaralkyl, phenyl or a radical of the above formula III, or $R_{15}$, conjointly with $R_{16}$, is trimethylene or tetramethylene, which is optionally substituted by a hydroxyl or oxo group and/or vicinally substituted by $R_{14}$ or a radical of the formula IV

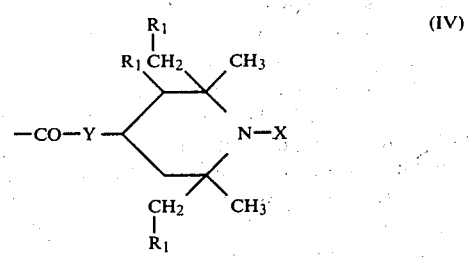

(IV)

in which X, Y, $R_1$ and $R_{14}$ have the above meaning, or, if n is 2, $R_{15}$ is a direct bond, $C_1$–$C_{20}$-alkylene, $C_2$–$C_{20}$-alkylene which is interrupted once or twice by —O—, —S—, —SO—, —$SO_2$— or —CO—O—, or $C_8$–$C_{14}$-arene-bis-alkylene, $C_4$–$C_8$-alkenylene or $C_4$–$C_8$-alkinylene, and their salts.

As $C_1$–$C_5$-alkyl, $R_1$ is for example, unbranched or branched alkyl, such as methyl, ethyl, n-propyl, isopropyl, n-butyl, isobutyl or isopentyl. Compounds to be mentioned amongst those which are preferred are those in which $R_1$ is methyl or ethyl, but above all hydrogen.

As alkyl, alkenyl and alkinyl, $R_4$ is, in particular, that indicated for X and as acyl is, in particular, that indicated for $R_{12}$.

As alkyl, alkenyl and alkinyl, $R_5$ is, in particular, that indicated for X and as phenylalkyl is, in particular, benzyl.

As acyl, $R_6$ is, in particular, that indicated for $R_{12}$.

The benzyl radical which carries $R_7$, $R_8$ and $R_9$ can be a para- or meta-hydroxybenzyl group. The substituents $R_7$ and $R_8$ located on the benzyl radical can be unbranched or branched alkyl groups with 1–9 C atoms, for example methyl, ethyl, isopropyl, tert.-butyl, n-hexyl, 1,1,3,3-tetramethylbutyl or tert.-nonyl. If $R_7$ or $R_8$ denotes cycloalkyl, this can be, for example, cyclopentyl, methylcyclopentyl, cyclohexyl or methylcyclohexyl. If $R_7$ or $R_8$ denotes aralkyl, this can be, for example, benzyl or α,α-dimethylbenzyl. $R_7$ and $R_8$ are preferably alkyl groups with 1–4 C atoms, especially methyl or tert.-butyl.

As $C_1$–$C_{12}$-alkyl, X is, for example, methyl, ethyl, n-propyl, n-butyl, n-pentyl, n-hexyl, n-octyl, n-decyl or n-dodecyl. Alkyl groups with 1–8 C atoms, and especially those with 1–4 C atoms, and above all methyl, are preferred.

As $C_3$–$C_6$-alkenyl, X is, for example, allyl, 2-butenyl or 2-hexenyl, especially allyl.

As $C_3$–$C_4$-alkinyl, X is, for example, propargyl.

If X denotes $C_2$–$C_{21}$-alkoxyalkyl, the alkyl part can contain 1–3 C atoms and the alkoxy part can consist of 1–18 C atoms, as in, for example, methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl. Compounds in which X denotes an alkoxyalkyl group with 2–6 C atoms are to be mentioned in particular.

As $C_7$–$C_8$-aralkyl, X is, for example, benzyl or α-phenylethyl.

As an aliphatic acyl group with 1–18 C atoms, X is, for example, formyl, acetyl, acryloyl or crotonoyl, especially acetyl.

As $C_1$–$C_{12}$-alkylaminocarbonyl, X is, in particular, such a radical containing n-alkyl radicals, above all with 1–6 C atoms, such as methylcarbamoyl, n-butylcarbamoyl or n-dodecylcarbamoyl, and as di-($C_1$–$C_{12}$)-alkylaminocarbonyl, X is, in particular, such a radical containing two different or, in particular, two identical n-alkyl radicals, each with 1–6 C atoms, such as dimethylcarbamoyl, diethylcarbamoyl or di-n-hexylcarbamoyl.

If X is the group $-CH_2COOR_{10}$, $R_{10}$, as $C_1$–$C_{12}$-alkyl, denotes, for example, methyl, ethyl, isopropyl, n-butyl, isobutyl, t-butyl, isopentyl, n-octyl, n-decyl or n-dodecyl. $R_{10}$ is preferably $C_1$–$C_4$-alkyl. As $C_3$–$C_6$-alkenyl, $R_{10}$ is, for example, allyl, 2-butenyl or 2-hexenyl. As $C_7$–$C_8$-aralkyl, $R_{10}$ is, for example benzyl or α-phenylethyl.

If X is the group $-CH_2-CH(R_{11})-OR_{12}$, $R_{11}$ denotes hydrogen, methyl or phenyl, especially hydrogen. As an aliphatic, aromatic, alicyclic or araliphatic $C_1$–$C_{18}$-acyl radical which is optionally substituted in the aromatic part by chlorine, $C_1$–$C_4$-alkyl, such as methyl, ethyl, n-propyl or t-butyl, or by $C_1$–$C_8$-alkoxy, such as methoxy, ethoxy, butoxy or octoxy, and/or by hydroxyl, $R_{12}$ is, for example, acetyl, propionyl, butyryl, octanoyl, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, β-(3,5-di-t-butyl-4-hydroxyphenyl)-propionyl, phenylacetyl, cinnamoyl, hexahydrobenzoyl, 1- or 2-naphthoyl or decahydronaphthoyl.

If X is the group $-COOR_{13}$, $R_{13}$, as $C_1$–$C_{12}$-alkyl, is, for example, methyl, ethyl, isobutyl, n-hexyl, n-octyl, n-decyl or n-dodecyl. Alkyl groups with 1–4 C atoms are preferred by $R_{13}$.

$R_{16}$ and $R_{17}$, as $C_1$–$C_{17}$-alkyl, have, in particular, the same meaning as X as alkyl, especially with 1–12 and preferably 1–18 C atoms, above all methyl, and as $C_7$–$C_9$-alkylphenyl have the meaning of, for example, methylphenyl, ethylphenyl or propylphenyl, and as $C_{11}$–$C_{14}$-(hydroxy)(alkyl)phenyl have the meaning of, in particular, 4-hydroxy-3,5-dialkyl-phenyl in which alkyl has in particular 1–8, and above all 1–4, C atoms, such as methyl or, in particular, tert.-butyl, and this also applies in the case of $C_{12}$–$C_{16}$-(hydroxy)(alkyl)phenylalkyl, and especially 4-hydroxy-3,5-dialkylbenzyl, -phenethyl or -β-phenylpropyl.

In the meaning of alkyl with 1–20 C atoms, $R_{15}$ can represent, for example, one of the alkyl groups listed above for X; it can also represent branched alkyl, such as isopropyl, isopentyl, 2-ethylbutyl, 2-ethylhexyl or isononyl or also a higher alkyl radical, such as, for example, n-hexadecyl, n-octadecyl or n-eicosyl.

When $R_{15}$ denotes a substituted or interrupted alkyl group it can be, for example, one of the following radicals: 2-phenoxyethyl, 2-benzyloxyethyl, 2-p-tolyloxypropyl, cyclohexyloxymethyl, 2-(β-naphthoxy)-ethyl, 2-phenylthioethyl, 2-(4-tert.-butylphenylthio)-ethyl, 2-acetylethyl, 2-isobutyrylethyl, 2-(dodecylcarbonyl)-ethyl, 2-cyanoethyl, cyanomethyl, 3-cyanopropyl, methoxycarbonylmethyl, dodecyloxycarbonylmethyl, 2-ethoxycarbonylethyl, 2-(cyclohexyloxycarbonyl)-ethyl, 2-(tert.-butoxycarbonyl)-ethyl, 2-(octadecyloxycarbonyl)-propyl, 4-(propoxycarbonyl)-butyl, 2-acetoxyethyl, 2-(isooctanoyloxy)-propyl, 2-(octadecanoyloxy)-ethyl, 2-(cyclopentylcarbonyloxy)-ethyl, 3-benzoyloxypropyl, 2-(p-tert.-butylbenzoyloxy)-ethyl, 2-salicyloyloxy-ethyl, 2-(3,5-di-tert.-butyl-4-hydroxybenzoyloxy)-ethyl, 2-phenylacetyloxyethyl, 2-(3,5-di-tert.-butyl-4-hydroxyphenylpropionyloxy)-propyl, diethylbutyl-phosphonomethyl, 2-dimethylphosphono-ethyl, 2-(dioctylphosphono)-ethyl, diphenylphosphonomethyl, 3-(diallylphosphono)-propyl, methoxymethyl, 2-butoxyethyl, 2-octadecyloxyethyl, isopropoxymethyl, 3-butylthio-propyl, 2-dodecylthio-ethyl, 2-(isohexylsulphinyl)-ethyl, 2-octadecylsulphonyl-ethyl or 2-ethylsulphonyl-propyl.

When $R_{15}$ denotes an alkenyl or alkinyl group it can be, for example, allyl, methallyl, 2-buten-1-yl, 3-hexen-1-yl, undecenyl, oleyl, propargyl or 2-heptin-1-yl.

Examples of $R_{15}$ as cycloalkyl, alkyl-cycloalkyl and cycloalkyl-alkyl are the cyclopentyl, cyclohexyl, cyclooctyl, cyclododecyl, methylcyclopentyl, dimethylcyclohexyl, propylcyclooctyl, hexylcyclododecyl, cyclohexylmethyl, 3-cyclooctylpropyl or decahydronaphthyl-α-methyl radicals.

Examples of $R_{15}$ as aralkyl and alkyl-aralkyl are the benzyl, 2-phenylethyl, 2-phenylpropyl, β-naphthylmethyl, 4-methylbenzyl, 4-t-butylbenzyl or 4-methylnaphthyl-1-methyl groups.

When n is 2, $R_{15}$ represents a direct bond or a divalent organic radical. The latter can be alkylene, such as, for example, methylene, ethylene or polymethylene with up to 20 C atoms, or the alkylene radical is interrupted by 1 or 2 heteromembers, such as, for example, the divalent radicals $-CH_2O-CH_2-$, $-CH_2C-H_2O-CH_2CH_2-$, $-CH_2CH_2-O-CH_2C-H_2-O-CH_2CH_2-$, $-(CH_2)_3-S-(CH_2)_3-$, $-CH_2CH_2-S-(CH_2)_4-S-CH_2CH_2-$, $-CH_2C-H_2-SO-CH_2CH_2-$, $-CH_2CH_2-SO_2-CH_2CH_2-$, $-CH_2CH_2-SO_2-(CH_2)_8-SO_2-CH_2CH_2-$, $-CH_2COOCH_2CH_2OOCCH_2-$, $-CH_2CH_2COOCH_2C-H_2OOCCH_2CH_2-$, $-CH_2CH_2-COO(CH_2)_4-OOC-CH_2CH_2-$, $-CH_2CH_2OCO(CH_2)_4COOCH_2CH_2-$ or $-CH_2CH_2OCO(CH_2)_8COOCH_2CH_2-$. $R_{15}$ can also be arene-bis-alkylene, such as, for example, p-xylylene, benzene-1,3-bis-(ethylene), diphenyl-4,4'-bis-(methylene) or naphthalene-1,4-bis-(methylene). Finally, it can be alkenylene or alkinylene with 4–8 C atoms, such as, for example, 2-butenylene-1,4, 2-butinylene-1,4 or 2,4-hexadiinylene-1,6.

Salts of compounds of the formula I are, in particular, acid addition salts with inorganic or organic acids. The salts can be obtained in the customary manner and the free bases, which are preferred, can be obtained again from the salts. Suitable acids for forming the salts are, in particular, inorganic acids, such as hydrochloric acid, sulphuric acid and phosphoric acid.

Compounds Ia of the formula I, in which n is 1 or 2, Y is oxy or imino, $R_1$ is hydrogen or $C_1$–$C_5$-alkyl, $R_2$ is a radical of the formula Ia or Ib, $R_3$ is hydrogen, $R_7$ and $R_8$ independently of one another are $C_1$–$C_4$-alkyl, $R_9$ is hydrogen, X is hydrogen, oxyl, $C_1$–$C_8$-alkyl, $C_3$–$C_4$-alkenyl or alkinyl, $C_2$–$C_6$-alkoxyalkyl, $C_7$–$C_8$-aralkyl, acetyl, acryloyl or crotonyl, or denotes one of the groups —$CH_2$—$COOR_{10}$, —$CH_2$—$CH(R_{11})$—$OR_{12}$ or —$COOR_{13}$, in which $R_{10}$ is $C_1$–$C_4$-alkyl, $C_3$–$C_4$-alkenyl, phenyl, $C_7$–$C_8$-aralkyl or cyclohexyl and $R_{11}$ is hydrogen, methyl or phenyl and $R_{12}$ denotes hydrogen or an aliphatic, aromatic, alicyclic or araliphatic acyl group with 1-18 C atoms, in which the aromatic part can optionally be substituted by chlorine, $C_1$–$C_4$-alkyl, $C_1$–$C_8$-alkoxy and/or hydroxyl, and $R_{13}$ is $C_1$–$C_{12}$-alkyl, $R_{14}$ is cyano, —$COOC_{1-4}$-alkyl, —$CO$—$R_{16}$ with the above meaning, —$SO_2$—$R_{17}$ with the above meaning or —$P(=O)(OR_{18})_2$ with the above meaning, and, when n=1, $R_{15}$ is hydrogen, a radical of the formula II with the above meaning, $C_1$–$C_{18}$-alkyl, $C_3$–$C_4$-alkenyl, propargyl, benzyl, phenyl, $C_1$–$C_4$-alkyl which is substituted by one of the groups —CN, —C(=O)$OR_{19}$, —O—C(=O)$R_{20}$ or —P(=O)(OR_{21})_2$ with the above meanings, or a radical of the formula III with the above meaning, or $R_{15}$, conjointly with $R_{16}$, is trimethylene or tetramethylene, which is optionally substituted as indicated above, or, when n=2, $R_{15}$ is $C_2$–$C_6$-alkylene or $C_8$–$C_{14}$-arene-bis-alkylene, are preferred.

Compounds Ib of the formula I, in which n is 1 or 2, Y is oxy or imino, $R_1$ is hydrogen or methyl, $R_2$ is a radical of the formula Ia or Ib, $R_3$ is hydrogen, $R_7$ and $R_8$ independently of one another are $C_1$–$C_4$-alkyl and $R_9$ is hydrogen and the benzyl radical which carries $R_7$, $R_8$ and $R_9$ is a 4—OH-benzyl, and X is hydrogen, $C_1$–$C_4$-alkyl, allyl, propargyl, $C_2$–$C_6$-alkoxyalkyl, acetyl, acryloyl or crotonoyl, or one of the groups —$CH_2$—$COOR_{10}$, —$CH_2$—$CH(R_{11})$—OH or —$COOR_{13}$ in which $R_{10}$ is $C_1$–$C_4$-alkyl, $R_{11}$ is hydrogen or methyl and $R_{13}$ is $C_1$–$C_4$-alkyl, $R_{14}$ is cyano, —$COOC_{1-4}$-alkyl, —$CO$-$R_{16}$ with the above meaning or —$SO_2$—$R_{17}$ with the above meaning and, when n=1, $R_{15}$ is hydrogen, 4—OH—3,5-di-$C_1$–$C_4$-alkyl-benzyl, $C_1$–$C_{12}$-alkyl, $C_3$–$C_4$-alkylene, propargyl, benzyl, phenyl or a radical of the formula V or VI

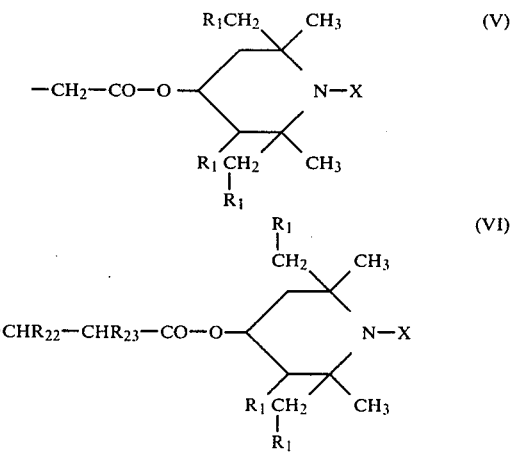

in which $R_1$ and X have the meaning given above under Ia, and $R_{22}$ and $R_{23}$ are hydrogen or methyl, or $R_{15}$, conjointly with $R_{16}$, is trimethylene or tetramethylene, which is optionally substituted as indicated above, or, when n=2, $R_{15}$ is $C_2$–$C_6$-n-alkylene or $C_8$–$C_{14}$-arene-bis-alkylene, are particularly preferred.

Compounds Ic of the formula I, wherein n is 1 or 2, Y is oxy or imino, $R_1$ is hydrogen or methyl, $R_2$ is a radical of the formula Ia or Ib, $R_3$ is hydrogen, $R_7$ and $R_8$ are methyl or tert.-butyl, $R_9$ is hydrogen and the benzyl which carries $R_7$, $R_8$ and $R_9$ is a 4—OH—benzyl, X is hydrogen, methyl, acetyl or acryloyl, $R_{14}$ is cyano, —$COOC_{1-4}$-alkyl or —$CO$—$R_{16}$ in which $R_{16}$ is $C_1$–$C_6$-alkyl or $C_1$–$C_6$-alkylsulphonyl, and, when n=1, $R_{15}$ is hydrogen, 4—OH—3,5-di-tert.-butyl-benzyl, $C_1$–$C_{12}$-n-alkyl, benzyl, phenyl, optionally N-methylated (2,2,6,6-tetramethyl-piperidinyl-4)-oxycarbonylmethyl or optionally N-methylated (2,3,6-triethyl-2,6-dimethyl-piperidinyl-4)-oxycarbonylmethyl, or $R_{15}$, conjointly with $R_{16}$, is trimethylene or tetramethylene, or, when n=2, $R_{15}$ is $C_2$–$C_6$-n-alkylene, are to be singled out above all.

Compounds to be singled out in particular amongst these are compounds Id of the formula I, in which n is 1, Y is oxy, $R_1$, $R_2$, $R_3$, $R_7$, $R_8$, $R_9$, X and $R_{15}$ have the meanings indicated under Ic and $R_{14}$ is cyano or —$CO$—$R_{16}$ in which $R_{16}$ is $C_1$–$C_6$-alkyl or, conjointly with $R_{15}$, is trimethylene or tetramethylene.

Examples of compounds of the formula I are: 1,2,2,6,6-pentamethyl-4-piperidinyl 2-butyl-2-(3,5-di-tert.-butyl-4-hydroxybenzyl)-acetoacetate, 1-acryloyl-2,6-diethyl-2,5,6-trimethyl-4-piperidinyl 2-dodecyl-(2,6-dimethyl-4-tert.-butyl-3-hydroxybenzyl)-acetoacetate, 2,2,6,6-tetramethyl-4-piperidinyl 2-(3,5-di-tert.-butyl-4-hydroxy-benzoyl)-2-(2,6-dimethyl-4-tert.-butyl-3-hydroxybenzene)-2-butyl-acetate, 1-propyl-2,2,6,6-tetramethyl-4-piperidinyl 5-(3,5-di-tert.-butyl-4-hydroxyphenyl)-3-oxo-2-(2,3-dimethyl-5-tert.-nonyl-4-hydroxybenzyl)-2-(2,2,6,6-tetramethyl-4-piperidinyloxy-carbonylmethyl)-pentanecarboxylate, bis-(3-methyl-5-α,α-dimethylbenzyl-4-hydroxybenzyl)-cyanoacetic acid (2,6-diethyl-1,2,5,6-tetramethyl-4-piperidinyl)-amide, 1-acetyl-2,3,6-trimethyl-2,6-diethyl-4-piperidinyl (3-tert.-butyl-5-tert.-amyl-4-hydroxybenzyl)-(2,2,6,6-tetramethyl-4-piperidinyloxy-carbonylethyl)-cyanoacetate, ethylene-bis-[3,3-[cyano-(2,2,6,6-tetramethyl-4-piperidinyloxy-carbonyl)]-4-(3,5-di-tert.-butyl-4-hydroxybenzyl)]-butyrate, 1-octyl-2,2,6,6-tetramethyl-4-piperidinyl (3,5-di-tert.-butyl-4-hydroxybenzyl)-cyclohexyl-cyanoacetate, 1,2,2,6,6-pentamethyl-4-piperidinyl 2-cyano-2-(2,3-dimethyl-5-tert.-butyl-4-hydroxybenzyl)-3-(1,2,2,6,6-pentamethyl-4-piperidinyloxy-carbonyl)-glutarate, 2,2,6,6-tetramethyl-4-piperidinyl 2-n-butyl-2-(2,6-dimethyl-4-tert.-butyl-3-hydroxybenzyl)-methylsulphonyl-acetate, 1-propionyl-2,2,6,6-tetramethyl-4-piperidinyl 3-tert.-butyl-5-tert.-amyl-4-hydroxybenzyl-methylsulphinyl-acetate, 2,3,6-trimethyl-2,6-diethyl-4-piperidinyl bis-(3-isopropyl-5-tert.-butyl-4-hydroxybenzyl)-phenylsulphonyl-acetate, 1-crotonyl-2,2,6,6-tetramethyl-4-piperidinyl 2-stearyl-2-(3-methyl-5-tert.-butyl-4-hydroxyphenyl)-benzylsulphonyl-acetate, 1,2,2,6,6-pentamethyl-4-piperidinyl 2-(1,2,2,6,6-pentamethyl-4-piperidinyloxycarbonylmethyl)-2-(2,6-dimethyl-4-tert.-butyl-3-hydroxybenzyl)-cyclohexylsulphonyl-acetate, 2,2,6,6-tetramethyl-4-piperidinyl 2-(diethyl phosphonate)-2-(3,5-di-tert.-butyl-4-hydroxybenzyl)-4-methyl-glutarate, 1,2,2,6,6-pentamethyl-4-piperidinyl bis-(3,5-di-tert.-butyl-4-hydroxybenzyl)-(1,2,2,6,6-pentamethyl-4- piperidinyloxy-carbonylmethyl)-nitroacetate, 1-acetyl-2,2,6,6-tetramethyl-4-piperidinyl 2-ethyl-2-(3,5-di-tert.-amyl-4-hydroxybenzyl)-di-(butyl phosphonate)-acetate, 1-acryloyl-2,3,6-trimethyl-2,6-diethyl-4-piperidinyl 2-n-octyloxy-carbonylmethyl-2-(3-methyl-5-cyclohexyl-4-hydroxybenzyl)-nitroacetate and 2,6-dimethyl-4-tert.-butyl-3-hydroxybenzyl-(diethyl phosphonate)-acetic acid (2,2,6,6-tetramethyl-4-piperidinyl)-amide.

The compounds of the formula I can be manufactured by various methods which consist of several individual steps in various sequences. The individual steps consist of reactions which are in themselves known. Thus, an acid or a reactive derivative, such as an ester, of the formula VII can be reacted with a piperidine VIII to give a compound IX:

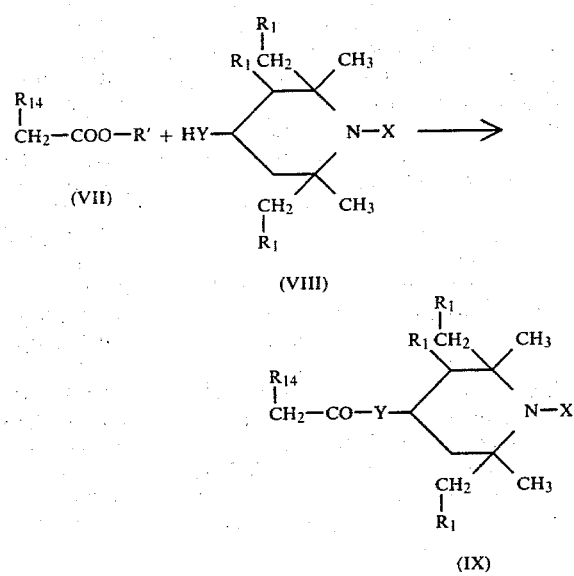

In this reaction, X can already be the substituent desired in the compound of the formula I; alternatively the tetramethylpiperidinol which is unsubstituted on the nitrogen, or 4-aminopiperidine (VIII, X=H) is used and the substituent X is introduced after the transesterification or in a later stage of the synthesis route. Polyalkyl-piperidinols and amines VIII in which X=H can be manufactured by reduction of the corresponding 4-piperidones, as is described, for example, in Japanese Patent Application 50–63,850.

X can be introduced by the customary methods for N-alkylation and N-acylation, for example by reaction with alkyl halides, alkenyl halides, propargyl chloride, benzyl chloride or carboxylic acid chlorides, preferably in the presence of molar amounts of a base.

Hydroxyalkyl radicals are introduced by reaction with epoxides, for example ethylene oxide or propylene oxide, and can be converted into the corresponding N-acyloxyalkyl groups by reaction with carboxylic acid chlorides or carboxylic acid anhydrides. When X is O, such N-oxyls can be manufactured from the NH compounds by oxidation with per-acids or hydrogen peroxide.

As the next step, either first the OH-benzyl substituent and then $R_{15}$ or—preferably—first the substituent $R_{15}$ and then OH-benzyl can be introduced into the compounds of the formula IX.

The introduction of the hydroxybenzyl group can be effected by reaction with a hydroxybenzyl dithiocarbamate of the formula HO-benzyl-S-CS-N(R")$_2$ in which R" denotes an alkyl group with 1–5 C atoms, or the two groups R", conjointly with the nitrogen, represent a morpholine, pyrrolidine or piperidine ring. Dithiocarbamates of this type are obtainable by reaction of a phenol with formaldehyde, carbon disulphide and a secondary amine.

The reaction of the dithiocarbamates with the activated methylene group in the compound IX is effected in a molar ratio of approximately 1:1 in the presence of basic reagents, such as alkali metal hydroxides, alkali metal alcoholates, alkali metal hydrides or alkaline earth metal hydrides or alkali metal amides. These bases are preferably used in molar amounts, that is to say approximately one equivalent of the base is added per mol of dithiocarbamate. The reaction can be carried out in solution, for example in alcohols, ethers or hydrocarbons. Polar aprotic solvents, such as dimethylformamide or dimethylsulphoxide, are also suitable. The reaction is preferably carried out in an alcoholic solution using an alkali metal hydroxide as the base.

Another suitable method for introducing the hydroxybenzyl group into the esters IX is to react the esters with hydroxybenzylamines OH-benzyl-N(R")$_2$. Amines of this type can be manufactured by reacting phenols with formaldehyde and a secondary amine in a so-called Mannich reaction. The reaction of the amines with the compounds IX is also accelerated with basic catalysts, preferably with alkali metal amides or alkali metal alcoholates. Alkali metals are also suitable as catalysts. In contrast to the dithiocarbamate process, however, catalytic amounts of, say, 0.1 to 5 mol %, of the basic catalyst suffice.

In place of the tertiary amines (Mannich bases) it is also possible to use the quaternisation products thereof. Solvents which can be used are those of the abovementioned categories but it is also possible to carry out the reaction without a solvent.

Finally, the OH-benzyl radical can also be introduced by converting the ester IX, with one equivalent of an alkali metal, alkali metal alcoholate, alkali metal amide or alkali metal hydride or of a similar basic alkali metal compound, into the alkali metal compound of IX, which is then reacted with 1 mol of a hydroxybenzyl halide (Hal=Cl, Br or I) in the customary manner. Although the two previously mentioned methods for hydroxybenzylation are preferred, the latter method can be of interest in those cases in which the halogen compound is readily accessible.

Each of the three methods mentioned leads to a hydroxybenzyl ester of the formula X into which the substituent $R_{15}$ can subsequently be introduced.

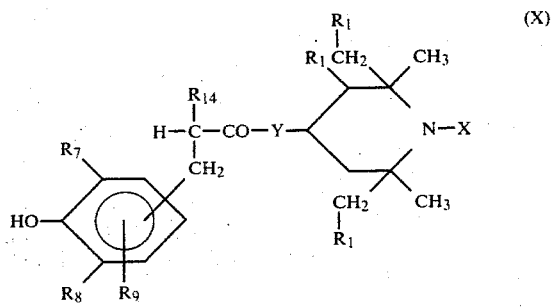

The introduction of the substituent $R_{15}$ can be effected by the classical method of C-alkylation of activated methylene compounds, in which method X is first converted into its alkali metal compound and then reacted with a halogen compound $R_{15}Hal$ or $R_{15}Hal_2$. In these formulae Hal again denotes Cl, Br or I. Depending on whether the aim is the synthesis of a compound of the formula I in which n is 1 or of a compound of the formula I in which n is 2, one mol of a monohalide $R_{15}Hal$ or half a mol of a dihalogen compound $R_{15}Hal_2$ is used per mol of the alkali metal compound of X. Examples of such halogen compounds are alkyl halides, cycloalkyl halides, aralkyl halides, alkenyl halides or alkinyl halides and alkylene dihalides, alkenylene dihalides, alkinylene dihalides or xylylene dihalides. Further examples are halogenocarboxylic acid esters, such as, for example, chloroacetates of monohydric or dihydric hydroxy compounds, or carboxylic acid esters of halogenohydrins, such as, for example, esters of 2-chloroethanol or 3-bromopropanol. Halogenophosphonates, such as, for example, dimethyl chloromethylphosphonate or diethyl 2-bromoethylphosphonate, are also suitable for this purpose.

If iodine is used in place of an organic halogen compound, compounds of the formula I in which $n=2$ and $R_{15}$ is a direct bond are obtained.

In addition to this classical method of C-substitution with halogen compounds, the method of the so-called Michael addition, in which compounds containing activated double bonds can be added on to the central C atom of the ester X, under the influence of basic catalysts, can be used to introduce the radical $R_{15}$. The best known variant is cyanoalkylation with acrylonitrile. However, esters of acrylic acid and methacrylic acid, vinyl ketones, vinyl sulphones, vinyl esters of carboxylic acids or esters of vinylphosphonic acid are also suitable. The catalysts used in this reaction are employed in amounts of about 0.5 to 5 mol %. Examples of catalysts which can be used are, again, alkali metal alcoholates, alkali metal amides, alkali metal hydrides or alkali metal hydroxides or quaternary ammonium bases, such as, for example, benzyltrimethylammonium hydroxide. Both in the case of the classical substitution and in the case of the process of the Michael addition, the reaction is preferably carried out in solution. Solvents which can be used are aprotic solvents, such as hydrocarbons or ethers, or polar solvents, such as, for example, benzene, toluene, dioxane, tetrahydrofurane or dimethylformamide.

One particular method for introducing phosphonomethyl groups as the substituent $R_{15}$ is to react X with formaldehyde and a diorgano phosphite of the formula $HP(O)(OR_{21})_2$.

Furthermore, a specific substituent $R_{15}$ can first be introduced by one of the said methods and this substituent is converted into another group $R_{15}$ in an additional reaction step. For example, the group $R_{15}$ —$CH_2CH_2COOC_2H_5$ can be introduced by an addition reaction with ethyl acrylate and this group is converted into the divalent group $R_{15}$ —$CH_2CH_2COOCH_2CH_2OOCCH_2CH_2$— in a second step by transesterification with ethylene glycol. In a similar manner, a halogenoalkyl group in an intermediate can be converted into a phenoxyalkyl or a phosphonoalkyl group. Alkylthioalkyl groups can be converted into the corresponding sulphoxides or sulphones by oxidation. Such an oxidation of the substituent $R_{15}$ can be effected at the same time as the introduction of oxygen as X, for example by oxidation with percarboxylic acids. When X and $R_{15}$ are identical, for example when they denote alkyl, alkenyl, propargyl or benzyl, the introduction of X can also be effected together with the introduction of $R_{15}$.

Because of these numerous possibilities for carrying out the individual reaction steps, that is to say the introduction of the piperidinyl radical, the introduction of the OH-benzyl group, the introduction of the group $R_{15}$ and, optionally, the introduction of X, the sequence of the individual steps will be chosen in the manner which seems most appropriate in a particular case. In the examples given below, the introduction of OH—benzyl is above all described as the final step. In principle, however, any other step can also be chosen as the final step.

Compounds of the formula I which contain the radical Ib can be obtained analogously to those with Ia. A corresponding piperidine which has a 2-hydroxyethyl group on the N atom is, for example, reacted with the ethyl ester of the acid $R_{14}CH_2COOH$, especially when hot, and the product is then hydroxybenzylated, alkylated or the like, for example as described above. When $R_{14}$ is acetyl it can also be suitable to use the diketene as the starting material. Compounds in which $R_{14}$ is acyl can be reduced to hydroxy compounds in the customary manner, for example using $NaBH_4$. If $R_{14}$ is —$COOC_{1-4}$-alkyl, the corresponding malonate is used as the starting material and is first transesterified on one side with the piperidinol and then substituted, as above.

The starting materials are known or, if they are new, can be obtained according to processes which are in themselves known.

Compounds of the formula VIII are known, for example the 4-OH compounds are known from German Offenlegungsschrift No. 2,352,658 and the 4-$NH_2$ compounds are known from U.S. Pat. No. 3,684,765. In general, the 4-OH compounds can be manufactured from the corresponding 4-oxopiperidines of the formula XI

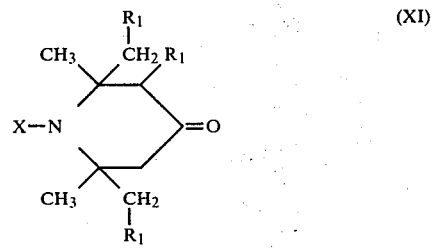

by reduction, for example catalytic hydrogenation over Raney nickel, whilst the 4-$NH_2$ compounds are obtainable from XI, for example by means of a reductive reaction with ammonia.

The 4-oxopiperidines of the formula XI, in which X is hydrogen, can be manufactured by various processes.

Thus, for example, the reaction of an aliphatic ketone with ammonia is described by W. Traube in Chem. Ber. 41, 777 (1908).

4-Oxopiperidines of the formula XI in which X denotes hydrogen can also be manufactured analogously to the process described in U.S. Pat. No. 3,513,170. In this reaction, a tetrahydropyrimidine which is substituted by alkyl is rearranged by hydrolysis in the presence of an acid catalyst.

N-H compounds of the formula XI, which possess substituents of different types in the 2-position and the 6-position, can be manufactured by reacting a ketone of the formula $R_1$—CO—$R_2$ with ammonia. The pyrimidine formed is hydrolysed as described in Helv. Chim. Acta 30, 114 (1947) to give an aminoketone of the formula XII

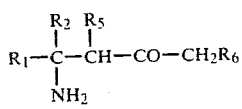 (XII)

The compounds of the formula XII are reacted, in a second process step, with ammonia and a ketone $R_3$—CO—$R_4$, as is described, for example, in Monatsh. Chemie 88, 464 (1957). The compounds of the formula XI, in which X denotes hydrogen, can be obtained from the pyrimidine, which results from this reaction, by hydrolysis.

Compounds of the formula XI in which X does not denote hydrogen can be manufactured from the corresponding N-H compounds by substitution. The reactions are the substitution reactions customary for secondary amines, although they proceed more slowly due to the steric hindrance of the radicals $R_1$-$R_4$. The N-H compounds can be reacted, for example, with alkyl halides, alkenyl halides, aralkyl halides or alkoxyalkyl halides, with dialkyl sulphates, with epichlorohydrins or with esters of chloro-carboxylic acids, such as chloroacetic acid esters, or acid chlorides or acid anhydrides.

The group —$CH_2$—$CH(R_{11})$—$OR_{12}$ can be introduced by reacting the N—H—piperidines with an epoxide of the formula

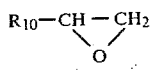

and subsequently acylating the reaction product with an acyl chloride of the formula $R_{12}Cl$.

Compounds of the 2,2,6,6-tetramethyl-4-(carbalkoxycyanomethyl)-piperidine type, which can be used as an intermediate product, are also known as intermediate products from British Patent Specification 1,214,426.

According to the present invention, the compounds of the formula I can be used as stabilisers for plastics, to protect them against damage due to the action of oxygen, heat and light. Examples of such plastics are the polymers listed on pages 12–14 of German Offenlegungsschrift 2,456,864.

The stabilisation of polyolefines and styrene polymers and of polyurethanes is of particular importance and the malonates of the formula I are outstandingly suitable for this. Examples of such polymers are high density polyethylene and low density polyethylene, polypropylene, ethylene-propylene copolymers, polystyrene, styrene-butadiene-acrylonitrile copolymers, mixtures of polyolefines or of styrene polymers and polyurethanes based on polyethers or polyesters, in the form of lacquers, elastomers or foams.

The stabilisers are added to the plastics in a concentration of 0.01 to 5% by weight, calculated relative to the material to be stabilised. Preferably, 0.03 to 1.5, and particularly preferentially 0.2 to 0.6%, by weight of the compounds, calculated relative to the material to be stabilised, are incorporated into the latter.

Incorporation can be effected after polymerisation, for example by mixing the compounds, and optionally further additives, into the melt by the methods customary in industry, before or during shaping, or by applying the dissolved or dispersed compounds to the polymer, if necessary with subsequent evaporation of the solvent.

The new compounds can also be added to the plastics to be stabilised in the form of a master batch which contains these compounds, for example in a concentration of 2.5 to 25% by weight.

In the case of crosslinked polyethylene, the compounds are added prior to crosslinking.

The invention therefore also relates to plastics stabilised by the addition of 0.01 to 5% by weight of a compound of the formula I, which plastics optionally can contain yet further known and customary additives. The plastics stabilised in this way can be used in very diverse forms, for example as sheets, fibres, tapes or profiles, or as binders for lacquers, adhesives or putties.

The manufacture and use of the compounds according to the invention will be described in more detail in the examples which follow. In these examples, parts denote parts by weight and % denotes percentages by weight. The temperatures are given in degrees centigrade.

Examples which may be mentioned of further additives, together with which the stabilisers which can be used according to the invention can be employed, are: antioxidants, such as simple 2,6-dialkylphenols, derivatives of alkylated hydroquinones, hydroxylated thiodiphenyl ethers, alkylidene-bisphenols, O—, N— and S—benzyl compounds, hydroxybenzylated malonates, hydroxybenzyl-aromatic compounds, s-triazine compounds, amides of β-(3,5-di-tert.-butyl-4-hydroxyphenyl)-propionic acid, esters of β-(3,5-di-tert.-butyl-4-hydroxyphenyl)-propionic acid, esters of β-(5-tert.-butyl-4-hydroxy-3-methylphenyl)-propionic acid, esters of 3,5-di-tert.-butyl-4-hydroxyphenylacetic acid, acylaminophenols, benzyl phosphonates and aminoaryl derivatives, UV absorbers and light protection agents, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of optionally substituted benzoic acids, and acrylates, and also nickel compounds, sterically hindered amines, oxalic acid diamides, metal deactivators, phosphites, compounds which destroy peroxide, polyamide stabilisers, basic C-stabilisers, PVC stabilisers, nucleating agents or other additives such as, for example, plasticisers, lubricants, emulsifiers, fillers, carbon black, asbestos, kaolin, talc, glass fibres, pigments, optical brighteners, flameproofing agents and antistatic agents.

Examples of further additives, together with which the stabilisers which can be used according to the invention can be employed, are given in German Offenlegungsschrift No. 2,427,853 on pages 18–24.

EXAMPLE 1

A solution of 1.60 g of NaOH in 20 ml of water is added dropwise, at 60° C., to a mixture of 2,2,6,6-tetramethyl-4-piperidinyl acetoacetate (4.82 g; 0.02 mol) and 3,5-di-t-butyl-4-hydroxybenzyl N,N-diethylcarbamate (14.7 g; 0.04 mol) in dimethylformamide (100 ml). After one night at 60°, the mixture is cooled to about 20° C. and 100 ml of water and then 100 ml of toluene are added. The organic phase is also washed with water and dried over MgSO₄. The solvent is then stripped off under reduced pressure. 8.2 g of 2,2,6,6-tetramethyl-4-piperidinyl 2,2-bis-(3,5-di-t-butyl-4-hydroxybenzyl)-acetoacetate, melting point 177°–178° C. (compound 1), are obtained from hexane/toluene.

The starting material is obtained analogously to the preparation of the starting material according to Example 2 but the reaction is preferably carried out without a catalyst. 2,2,6,6-Tetramethyl-4-piperidinyl acetoacetate boils at 105° C./0.5 mm Hg.

EXAMPLE 2

If 2,2,6,6-tetramethyl-4-piperidinyl cyanoacetate is used in Example 1, 2,2,6,6-tetramethyl-4-piperidinyl 2,2-bis-(3,5-di-tert-butyl-4-hydroxybenzyl)-cyanoacetate, which has a melting point of 174° C. (compound 2), is obtained.

The starting material is obtained as follows:

33.8 g (0.3 mol) of ethyl cyanoacetate and 47.1 g (0.3 mol) of 4-hydroxy-2,2,6,6-tetramethylpiperidine are dissolved in 50 ml of xylene. The mixture is warmed to 128° C., 0.3 g of lithium amide are added and the temperature is kept at 128° C. until the bulk of the ethanol has distilled off. The temperature is kept at 140°–150° C. for a further 3 hours and in this way the total xylene is stripped off after applying a vacuum. The residue is neutralised with glacial acetic acid and, after recrystallisation from ligroin, 2,2,6,6-tetramethyl-4-piperidinyl cyanoacetate, which has a melting point of 120° C., is obtained.

EXAMPLE 3

If 3-methyl-4-hydroxy-5-t-butyl-benzyl N,N-diethylcarbamate and 2,2,6,6-tetramethyl-4-piperidinyl 2-(2,2,6,6-tetramethyl-4-piperidinyl-cyanoacetate are used in Example 1, 2,2,6,6-tetramethyl-4-piperidinyl-2-(2,2,6,6-tetramethylpiperidinyl)-2-(3-methyl-5-tert-butyl-4-hydroxybenzyl)-cyanoacetate which has a melting point of 180°–182° C. (compound 3) is obtained.

The starting material is obtained as follows:

155 g (1 mol) of triacetonamine, 113 g of ethyl cyanoacetate, 300 ml of benzene and 31 g of ammonium acetate are kept under reflux for 1.5 hours under a water separator. The benzene phase is treated with 50% of potassium carbonate, the organic phase is dried over sodium sulphate and the benzene is then stripped off in vacuo. Ethyl 2,2,6,6-tetramethyl-4-piperidinylidenecyanoacetate is obtained as an oily residue.

This ester is hydrogenated over Pd/C in ethanol and gives ethyl 2-(2,2,6,6-tetramethyl-4-piperidinyl)-cyanoacetate which has a melting point of 116°–117° C.

The transesterification to give 2,2,6,6-tetramethyl-4-piperidinyl 2-(2,2,6,6-tetramethyl-4-piperidinyl)-cyanoacetate, which has a melting point of 116°–117° C., is carried out analogously to Example 2.

EXAMPLE 4

Analogously to Example 3, 2,2,6,6-tetramethyl-4-piperidinyl 2-(2,2,6,6-tetramethylpiperidinyl)-2-(3,5-di-t-butyl-4-hydroxybenzyl)-cyanoacetate, which has a melting point of 130° C. (compound 4), is obtained using 3,5-di-t-butyl-4-hydroxybenzyl N,N-diethylcarbamate.

EXAMPLE 5

A mixture of 2-(2,2,6,6-tetramethyl-4-piperidinyloxycarbonyl)-cyclohexanone (42.2 g; 0.15 mol) and N-(3,5-di-t-butyl-4-hydroxybenzyl)-dimethylamine (39.5 g; 0.15 mol) in ligroin (75 ml) is heated to 80°. After adding lithium amide (0.3 g), the mixture is heated under reflux for 12 hours. After cooling, 40 ml of ligroin, and also acetic acid (0.9 g), are added and the product is then filtered off and washed with a little ligroin. This gives 2-(3,5-di-t-butyl-4-hydroxybenzyl)-2-(2,2,6,6-tetramethyl-4-piperidinyloxycarbonyl)-cyclohexanone (compound 5); melting point 178°–181° C.

The starting material is obtained as follows:

2-Ethoxycarbonyl-cyclohexanone is transesterified with 4-hydroxy-2,2,6,6-tetramethyl-piperidine analogously to Example 2.

EXAMPLE 6

A mixture of 2,2,6,6-tetramethyl-4-piperidinyl t-butylsulphonyl-acetate (15.9 g; 0.05 mol) and N-(3,5-di-t-butyl-4-hydroxybenzyl)-dimethylamine (13.2 g; 0.05 mol) in ligroin is heated to 80°. After adding 60 mg of LiNH$_2$, the mixture is stirred under reflux for 12 hours. 180 mg of acetic acid in 10 ml of ligroin are added to the cooled suspension. 14.8 g of 2,2,6,6-tetramethyl-4-piperidinyl 2-(3,5-di-t-butyl-4-hydroxybenzyl)-t-butylsulphonylacetate (compound 6) which has a melting point of 124°–125° C. are obtained from hexane.

The starting material is obtained as follows:

38.8 g (0.2 mol) of methyl t-butylsulphonyl-acetate, prepared according to the method of von Leusen and Strating, Rec. Trav, Chim. 84, 140 (1965), and 31.4 g (0.2 mol) of 4-hydroxy-2,2,6,6-tetramethylpiperidine are dissolved in 50 ml of xylene. The mixture is warmed to 130°, 0.2 g of lithium amide in 50 ml of xylene is added and the mixture is stirred for 12 hours at 130°–140°. The xylene is removed in vacuo and the residue is distilled to give 2,2,6,6-tetramethyl-4-piperidinyl t-butyl-sulphonyl-acetate; yield: 33.7 grams, boiling point 153°–154°/10$^{-3}$ mm Hg.

If the procedure followed is as described in Example 1, the following compounds are obtained:

EXAMPLE 7

1,2,2,6,6-Pentamethyl-4-piperidinyl 2,2-bis-(3,5-di-t-butyl-4-hydroxybenzyl)-acetoacetate (compound 7), melting point 154°–157° C.

The starting material is obtained as follows:

Ethyl acetoacetate is transesterified with 4-hydroxy-1,2,2,6,6-pentamethyl-piperidine analogously to Example 2.

EXAMPLE 8

1,2,2,6,6-Pentamethyl-4-piperidinyl 2,2-bis-(3,5-di-t-butyl-4-hydroxybenzyl)-cyanoacetate (compound 8), melting point 185° C.

EXAMPLE 9

2,3,6-Trimethyl-2,6-diethyl-4-piperidinyl 2,2-bis-(3,5-di-t-butyl-4-hydroxybenzyl)-cyanoacetate (compound 9), melting point 90°–95° C.

EXAMPLE 10

2,2-Bis-(3,5-di-t-butyl-4-hydroxybenzyl)-acetoacetic acid (2,2,6,6-tetramethyl-4-piperidinyl)-amide (compound 10), melting point 189°–191° C.

EXAMPLE 11

2,2,6,6-Tetramethyl-4-piperidinyl 2-(3,5-di-t-butyl-4-hydroxybenzyl)-2-(sec.-butyl)-cyanoacetate (compound 11), melting point 106°–108° C.

EXAMPLE 12

2-(3,5-Di-t-butyl-4-hydroxybenzyl)-2,5-bis-(2,2,6-tetramethyl-4-piperidinyloxycarbonyl)-1,4-cyclohexanedione (compound 12), melting point 210° C. (decomposition).

EXAMPLE 13

2,2,6,6-Tetramethyl-4-piperidinyl 3,5-di-t-butyl-4-hydroxybenzyl-(diethyl phosphonate)-acetate (compound 13), melting point 108°–109° C.

EXAMPLE 14

198.2 g (1.5 mols) of dimethyl malonate and 95.5 g (0.05 mol) of 1,2,2,6,6-pentamethyl-4-hydroxypiperidine are warmed to an internal temperature of 125° C. 1 g of $LiNH_2$ is added and the mixture is slowly warmed to 135°–140° C., whilst distilling off the methanol. After 5 hours the reaction has ended, the reaction mixture is neutralised with glacial acetic acid, the residue is taken up in toluene and the organic phase is washed with water and dried over $Na_2SO_4$. After stripping off the solvent in vacuo and distilling the residue, monomethyl mono-1,2,2,6,6-pentamethyl-4-piperidinyl malonate with a boiling point/0.02 mm Hg of 107°–109° C. is obtained.

If the above compound is alkylated, as described under Example 1, with 3,5-di-t-butyl-4-hydroxybenzyl N,N-diethylcarbamate, this gives monomethyl mono-1,2,2,6,6-pentamethyl-4-piperidinyl bis-(3,5-di-t-butyl-4-hydroxybenzyl)-malonate with a melting point of 175° C. (compound 14).

Transesterification and alkylation as described under Example 14 give the following compounds:

EXAMPLE 15

Monomethyl mono-2,2,6,6-tetramethyl-4-piperidinyl bis-(3,5-di-t-butyl-4-hydroxybenzyl)-malonate with a melting point of 191°–192° C. (compound 15).

EXAMPLE 16

Monoethyl mono-2,2,6,6-tetramethyl-4-piperidinyl n-butyl-(3,5-di-t-butyl-4-hydroxybenzyl)-malonate as an oily residue (compound 16).

Analysis: found N, 2.7%; Calculated N, 2.57%.

EXAMPLE 17

Monoethyl mono-1,2,2,6,6-pentamethyl-4-piperidinyl n-butyl-(3,5-di-t-butyl-4-hydroxybenzyl)malonate as an oily residue (compound 17).

Analysis: Found C, 73.2%; H, 10.5%; N, 2.7%; Calculated C, 72.95%; H, 10.26%; N, 2.5%.

EXAMPLE 18

Monoethyl mono-1,2,2,6,6-pentamethyl-4-piperidinyl isopropyl-(3,5-di-t-butyl-4-hydroxybenzyl)-malonate as an oily residue (compound 18).

Analysis: Found N, 2.5%; Calculated N, 2.57%.

EXAMPLE 19

The monoethyl ester of bis-(3,5-di-t-butyl-4-hydroxybenzyl)-malonic acid mono-2,2,6,6-tetramethyl-4-piperidinylamide with a melting point of 204° C. (compound 19).

EXAMPLE 20

Monoethyl mono-2-(2,2,6,6-tetramethylpiperidino)-ethyl bis-(3,5-di-t-butyl-4-hydroxybenzyl)-malonate with a melting point of 100° C. (compound 20).

EXAMPLE 21

Monoethyl mono-2-(2,2,6,6-tetramethylpiperidino)-ethyl n-butyl-(3,5-di-t-butyl-4-hydroxybenzyl)-malonate as an oily residue (compound 21).

Analysis: Found N, 2.7%; Calculated N, 2.44%.

EXAMPLE 22

A solution of 2,2,6,6-tetramethyl-4-piperidinyl 2,2-bis-(3,5-di-tert-butyl-4-hydroxybenzyl)-acetoacetate (Example 1, 10.0 g; 0.015 mol) in 100 ml of acetic anhydride is stirred for 20 hours at 100°. The mixture is concentrated in vacuo. After recrystallisation from hexane/toluene, the product is filtered off and 8.41 g of 1-acetyl-2,2,6,6-tetramethyl-4-piperidinyl 2,2-bis-(3,5-di-tert-butyl-4-hydroxybenzyl)-acetoacetate, melting point 165°–166° C. (compound 22), are obtained.

EXAMPLE 23

1-Formyl-2,2,6,6-tetramethyl-4-piperidinyl 2,2-bis-(3,5-di-t-butyl-4-hydroxybenzyl)-acetoacetate, melting point 159° C. (compound 23), is obtained analogously to Example 22 using the mixed anhydride of acetic acid and formic acid.

EXAMPLE 24

1-Formyl-2,2,6,6-tetramethyl-4-piperidinyl 2,2-bis-(3,5-di-t-butyl-4-hydroxybenzyl)-cyanoacetate with a melting point of 182°–187° C. (compound 24) is obtained analogously to Example 23.

EXAMPLE 25

49.9 g (0.1 mol) of 2-(3,5-di-tert.-butyl-4-hydroxybenzyl)-2-(2,2,6,6-tetramethyl-4-piperidinyloxycarbonyl)-cyclohexanone (compound 5) are reduced by methods known from the literature with 1 g of $NaBH_4$ to give 2-(3,5-di-t-butyl-4-hydroxybenzyl)-2-(2,2,6,6-tetramethyl-4-piperidinyloxycarbonyl)-cyclohexanol, melting point 187°–190° C. (compound 25).

EXAMPLE 26

100 parts of polypropylene (melt index 3.2 g/10 minutes, 230°/2,160 g) are mixed intensively for 10 minutes, in a shaking apparatus, with 0.2 part of one of the additives listed in Table 1 which follows. The resulting mixture is kneaded for 10 minutes at 200° in a Brabender plastograph and the composition obtained in this way is then pressed in a platen press at a platen temperature of 260° to give 1 mm thick sheets, from which strips 1 cm broad and 17 cm long are punched.

The effectiveness of the adjuvant added to the test strips is tested by heat-ageing in a circulating air oven at 135° and 149°, a test strip which is free from additives serving as a comparison. Three test strips from each formulation are employed for the test. The end point is defined as the start of readily visible crumbling of the test strip. The results are given in Table 1.

Table 1

| Compound | Days until the start of decomposition | |
|---|---|---|
| | at 149° | at 135° |
| 1 | 72 | 14 |
| 23 | 32 | 6 |
| 10 | 32 | 6 |
| 7 | 23 | 6 |
| 5 | 49 | 17 |
| 12 | 39 | 9 |
| 2 | 69 | 20 |
| 8 | — | 17 |
| 11 | 9 | 1 |
| 4 | 36 | 7 |
| 3 | 33 | 7 |
| 6 | 12 | 1 |
| 13 | 13 | 2 |
| 26 | 49 | 12 |

Table 1-continued

| Compound | Days until the start of decomposition | |
|---|---|---|
| | at 149° | at 135° |
| 23 | 32 | 6 |
| 17 | 33 | 5 |
| 14 | | 19 |

EXAMPLE 27

100 parts of polypropylene powder (Moplen, Fibre grade, from Messrs. Montedison) are homogenised for 10 minutes at 200° C., in a Brabender plastograph, with 0.2 part of octadecyl β-(3,5-di-tert-butyl-4-hydroxyphenyl)-propionate and 0.25 part of one of the stabilisers in the table which follows. The composition thus obtained is removed from the kneader as rapidly as possible and pressed in a toggle press to give a 2–3 mm thick sheet. Part of the resulting pressed blank is cut out and pressed between two high-gloss hard aluminium foils, using a manual hydraulic laboratory press, for 6 minutes at 260° and under a pressure of 12 tonnes to give a 0.5 mm thick sheet, which is immediately chilled in cold water. The 0.1 mm thick test sheet is produced from this 0.5 mm sheet under precisely the same conditions. 60×44 mm portions are now punched from this test sheet and exposed in the Xenotest 150. These test pieces are taken from the exposure apparatus at regular intervals and their carbonyl content is tested in a IR spectrophotometer. The increase in the carbonyl extinction on exposure is a measure of the photo-oxidative degradation of the polymer (see L. Balaban et al., J. Polymer Sci, Part C, 22, 1059–1071 (1969); J. F. Heacock, J. Polymer Sci. Part A-1, 22, 2921–34 (1969) and D. J. Carlsson and D. M. Wiles, Macromolecules 2, 587–606 (1969)) and, according to experience, is associated with a deterioration in the mechanical properties of the polymer. The time taken to reach a carbonyl extinction of about 0.3, at which the comparison sheet is brittle, is taken as a measure of the protective action.

The protective action of the stabilisers according to the invention can be seen from Table 2 which follows:

Table 2

| Stabiliser Example No. | Time of exposure in hours until the carbonyl extinction is 0.300 |
|---|---|
| none | 1400 |
| 1 | 3280 |
| 2 | 5280 |
| 6 | 3270 |
| 15 | 5150 |
| 23 | 1940 |

The invention also relates to the starting materials of the formulae IX and X, their manufacture and their use as stabilisers and as intermediate products for the manufacture of the compounds of the formula I, and to organic material which has been stabilised, with these starting materials, against thermooxidative and/or light-induced degradation.

The symbols in compounds IX have the above meaning, especially the meaning indicated above as being preferred. In particular the meanings are those according to compounds Ia–Id and for compounds IX they can be seen from the starting materials in the illustrative examples.

The starting materials of the formula VII are known, as are those of the formula VIII and the manufacture of these substances is also described above. The compounds of the formula IX are distinguished, in particular, by a light-protection action. The substrates which can be stabilised with these compounds are those mentioned above and the above co-stabilisers can also be used. The amount of stabiliser corresponds to the above data. In particular, however, the compounds of the formula IX are suitable for the manufacture of compounds of the formula I, as described above.

What is claimed is:

1. A member selected from the group consisting of (A) a compound of the formula

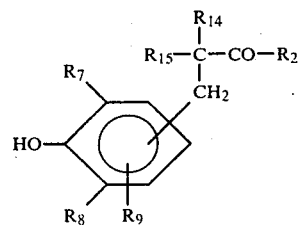

in which $R_2$ represents

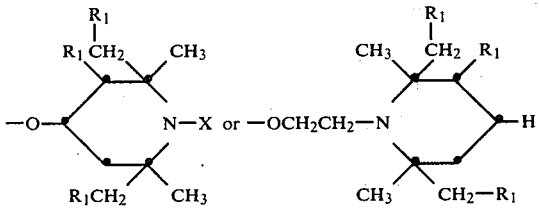

$R_1$ is hydrogen or $C_1$–$C_5$-alkyl, $R_7$ and $R_8$ independently represent $C_1$–$C_9$-alkyl, $C_7$–$C_9$-aralkyl or $C_5$–$C_8$-cycloalkyl, $R_9$ is hydrogen or methyl, X represents (1) hydrogen, (2) $C_1$–$C_4$ alkyl, (3) allyl, (4) propargyl, (5) $C_2$–$C_6$ alkoxyalkyl, (6) acetyl, (7) acryloyl, (8) crotonoyl, (9) —$CH_2$—$COOR_{10}$ where $R_{10}$ is $C_1$–$C_4$ alkyl, (10) —$CH_2$—$CH(R_{11})$—OH where $R_{11}$ is H or methyl or (11) —$COOR_{13}$ where $R_{13}$ is $C_1$ to $C_4$ alkyl, $R_{14}$ is cyano, $C_1$–$C_4$ alkyl, or $C_1$ to $C_6$ alkyl sulphonyl, $R_{15}$ is (1) hydrogen, (2) 4—OH-3,5-di $C_1$ to $C_4$ alkyl benzyl, (3) $C_1$ to $C_{12}$ alkyl, (4) $C_3$ to $C_4$ alkenyl, (5) propargyl, (6) benzyl, (7) phenyl, (8) a group of the formula

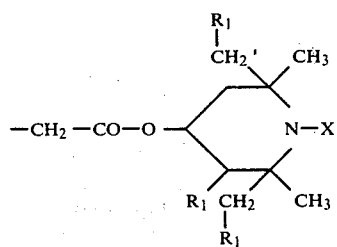

wherein $R_1$ and X are as previously defined, or (9) a group of the formula

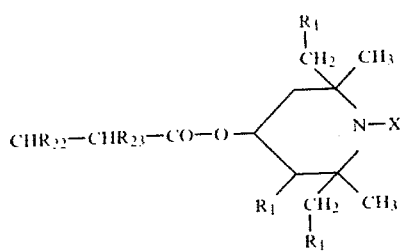

wherein $R_1$ and X are as previously defined and $R_{22}$ and $R_{23}$ are H or methyl, and (B) an acid addition salt thereof with an organic or inorganic acid.

2. A compound according to claim 1, of the formula

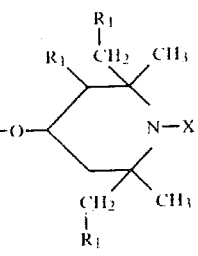

wherein $R_1$, $R_7$, $R_8$, $R_9$, X, $R_{14}$ and $R_{15}$ are as defined in claim 1.

3. A compound according to claim 1, said compound being 1,2,2,6,6-pentamethyl-4-piperidinyl 2,2-bis-(3,5-di-t-butyl-4-hydroxy benzyl)cyanoacetate.

* * * * *